(12) United States Patent
Song et al.

(10) Patent No.: US 8,994,715 B2
(45) Date of Patent: Mar. 31, 2015

(54) 3D IMAGE DISPLAY APPARATUS

(75) Inventors: Hoon Song, Yongin-si (KR); Yoon-sun Choi, Yongin-si (KR); Hong-seok Lee, Seongnam-si (KR); Jung-mok Bae, Seoul (KR); Kyu-hwan Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 278 days.

(21) Appl. No.: 13/482,670

(22) Filed: May 29, 2012

(65) Prior Publication Data
US 2012/0306726 A1 Dec. 6, 2012

(30) Foreign Application Priority Data

Jun. 2, 2011 (KR) .......................... 10-2011-053366

(51) Int. Cl.
G09G 3/00 (2006.01)
G06T 15/00 (2011.01)
G01N 33/483 (2006.01)
H04N 13/04 (2006.01)

(52) U.S. Cl.
CPC ....... *G01N 33/4836* (2013.01); *H04N 13/0418* (2013.01); *H04N 13/0406* (2013.01); *G09G 3/003* (2013.01)

USPC .......................................... 345/214

(58) Field of Classification Search
CPC ........... G09G 3/346; G09G 3/00; G09G 3/34; G09G 5/00; G02F 1/00; G02F 1/03; G02B 27/22
USPC .............................. 345/32, 205, 211; 359/359
See application file for complete search history.

(56) References Cited

U.S. PATENT DOCUMENTS

| | | | |
|---|---|---|---|
| 7,425,069 B2 | 9/2008 | Schwerdtner et al. | |
| 7,466,733 B2 * | 12/2008 | Nishida | 372/38.05 |
| 7,786,953 B2 * | 8/2010 | Saishu | 345/4 |
| 2008/0123182 A1 * | 5/2008 | Cernasov | 359/359 |
| 2011/0025657 A1 * | 2/2011 | Pakhchyan et al. | 345/205 |
| 2011/0109964 A1 * | 5/2011 | Kim et al. | 359/463 |

* cited by examiner

*Primary Examiner* — Andrew Sasinowski
(74) *Attorney, Agent, or Firm* — NSIP Law

(57) ABSTRACT

A 3D image display apparatus is provided. The 3D image display apparatus includes a light emission unit including one or more cells, the cells being configured to respectively adjust a direction in which light is emitted, an active prism array on the light emission unit, the active prism array including one or more prism units corresponding to the cells, the active prism array being configured to adjust an inclination of a refracting surface of each of the prism units according to an electric signal to change an optical path, and a display panel configured to modulate light that passes through the active prism array according to an image signal to form an image.

19 Claims, 8 Drawing Sheets

3D IMAGE DISPLAY APPARATUS

CROSS-REFERENCE TO RELATED APPLICATIONS

This application claims the benefit of Korean Patent Application No. 10-2011-0053366, filed on Jun. 2, 2011, in the Korean Intellectual Property Office, the entire disclosure of which is incorporated herein by reference for all purposes.

BACKGROUND

1. Field

The following description relates to a 3D image display apparatus having a wide viewing angle by adjusting a direction in which light is emitted.

2. Description of Related Art

The 3D image display apparatus is considered by many to be the "next generation" flat panel display device. A three-dimensional (3D) image of a 3D image display apparatus is realized by implementing the principle of stereoscopic vision. The principle of stereoscopic vision provides that both eyes of a human being see an object at the same time.

Binocular parallax is a characteristic that occurs because of the left eye and right eye being positioned about 65 mm apart. Binocular parallax is the most important factor producing a 3D effect.

3D image displays are generally classified into displays that require the use of glasses to view 3D images and displays that do not require the use of glasses to view 3D images. Displays that do not require the use of glasses to view 3D images divide an image into an image for the left eye and an image for the right eye. Displays that do not require the use of glasses to view 3D images are classified into parallax barrier-type displays and lenticular-type displays.

The parallax barrier-type display alternately displays images that should be seen respectively by the left and right eyes in the form of a vertical pattern or a photo using an extremely thin vertical lattice column, i.e., a barrier. By doing so, a vertical pattern image that is to be provided to the left eye and a vertical pattern image that is to be provided to the right eye are separated by the barrier. Images are thereby seen by the left and the right eyes from different viewpoints, respectively, so that a stereo image is perceived.

The lenticular-type display arranges images corresponding to the left and right eyes on a focusing surface of a lenticular lens. When the left and right eyes observe the images through the lenticular lens, the arranged images are incident to the left and right eyes according to a directivity feature of the lens so that a stereo image is perceived.

However, in both the parallax barrier-type display and the lenticular-type display, a period, a focal length, and a direction of the barrier or the lens are fixed, thereby serving to limit ranges in which 3D images are seen. For example, the direction in which the 3D images are seen is set according to the arrangement direction of the lenticular lens or the barrier. Thus, the 3D images may be seen in only one of a transverse mode and a longitudinal mode. In addition, resolution is reduced according to the number of views in the parallax barrier-type display or the lenticular-type display.

SUMMARY

In one general aspect, there is provided a 3D image display apparatus, including a light emission unit including one or more cells, the cells being configured to respectively adjust a direction in which light is emitted, an active prism array on the light emission unit, the active prism array including one or more prism units corresponding to the cells, the active prism array being configured to adjust an inclination of a refracting surface of each of the prism units according to an electric signal to change an optical path, and a display panel configured to modulate light that passes through the active prism array according to an image signal to form an image.

The general aspect of the 3D image display apparatus may further provide that the light emission unit is further configured to adjust an angle by which light is emitted from the light emission unit, a range of incidence angle of light incident to the active prism array is dependent upon the adjusted angle, and a range within which an angle of light emission is changed is dependent upon the range of incidence angle of light and the adjusted angle.

The general aspect of the 3D image display apparatus may further provide that the adjusted inclination of the refracting surface of each of the prism units is dependent upon the adjusted direction in which light is emitted.

The general aspect of the 3D image display apparatus may further provide that a direction in which light is emitted from the active prism array is dependent upon the adjusted direction in which light is emitted and the adjusted inclination of the refracting surface of each of the prism units.

The general aspect of the 3D image display apparatus may further provide that the display panel is between the light emission unit and the active prism array.

The general aspect of the 3D image display apparatus may further provide that the display panel is on the light emission unit and the active prism array.

The general aspect of the 3D image display apparatus may further provide that the light emission unit includes a light guide plate configured to guide light emitted from a light source, a shutter array on the light guide plate, the shutter array including one or more shutters, the shutters being grouped to respectively correspond to each of the cells, each of the shutters being independently openable and closeable, and a lens array on the shutter array.

The general aspect of the 3D image display apparatus may further provide that the light emission unit further includes the light source.

The general aspect of the 3D image display apparatus may further provide that the shutter array includes a liquid crystal shutter, an electric wetting shutter, or a frustrated total internal reflection (FTIR) shutter.

The general aspect of the 3D image display apparatus may further provide that the shutter array is arranged in a two-dimensional structure.

The general aspect of the 3D image display apparatus may further provide that the shutter array is on a focal plane of the lens array.

The general aspect of the 3D image display apparatus may further provide that the lens array includes one or more lenses corresponding to each of the cells, each of the lenses being configured to limit a proceeding direction of light emitted from a respective grouping of the shutters.

The general aspect of the 3D image display apparatus may further provide a controller having data, the data including relations between opening and closing operations of the shutters and the adjusted inclination of the refracting surface of each of the prism units.

The general aspect of the 3D image display apparatus may further provide that the light emission unit includes a light source array comprising one or more light sources, the light sources being grouped to respectively correspond to each of the cells, each of the light sources being independently turned on and turned off, and a pin hole array including one or more pin holes corresponding to each of the cells, each of the pin holes being configured to limit a proceeding direction of light emitted from a respective grouping of the light sources.

The general aspect of the 3D image display apparatus may further provide that the light emission unit includes one or more reflection units respectively grouped in a curved surface shape in each of the cells, each of the reflection units having a curved surface shape, each of the reflection units having a light source disposed thereon.

The general aspect of the 3D image display apparatus may further provide that each of the reflection units reflect light emitted from the light source as collimated light.

The general aspect of the 3D image display apparatus may further provide that the light source of each of the reflection units is independently turned on and turned off.

The general aspect of the 3D image display apparatus may further provide that each of the prism units includes a first electrode and a second electrode facing each other, a first hydrophobic layer on an inner wall of the first electrode, a second hydrophobic layer on an inner wall of the second electrode, a first medium between the first electrode and the second electrode, and a second medium between the first electrode and the second electrode, the second medium having a refractive index that is different from a refractive index of the first medium.

The general aspect of the 3D image display apparatus may further provide that the first medium includes a polarizing liquid, and the second medium includes a non-polar liquid.

The general aspect of the 3D image display apparatus may further provide that the refracting surface includes a boundary between the first medium and the second medium.

Other features and aspects may be apparent from the following detailed description, the drawings, and the claims.

Figure 1:
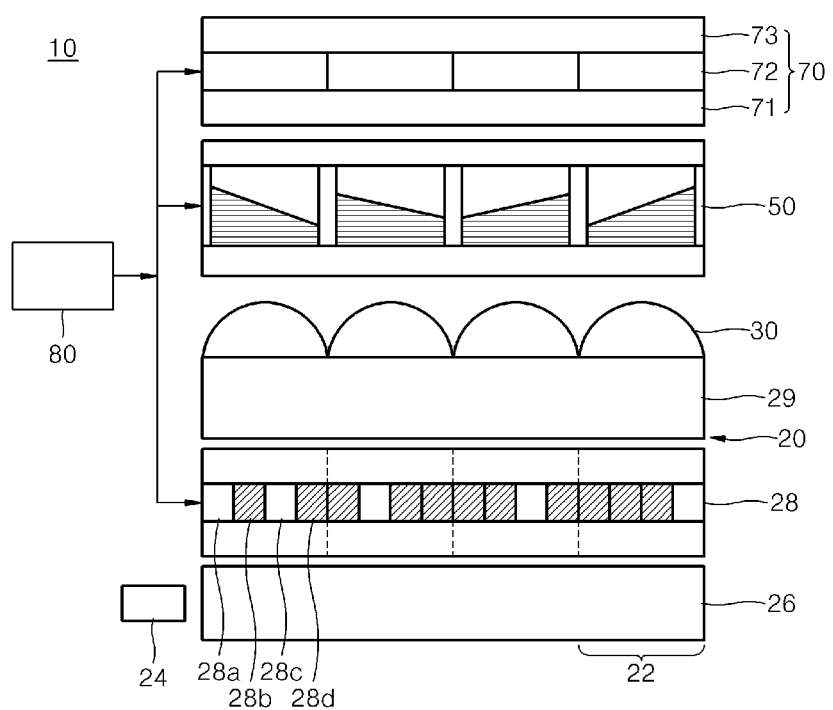
FIG. 1 is a schematic view illustrating a 3D image display apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. In addition, descriptions of well-known functions and constructions may be omitted for increased clarity and conciseness.

It is understood that the features of the present disclosure may be embodied in different forms and should not be constructed as limited to the example embodiment(s) set forth herein. Rather, embodiment(s) are provided so that this disclosure will be thorough and complete, and will convey the full scope of the present disclosure to those skilled in the art. The drawings may not be necessarily to scale, and, in some instances, proportions may have been exaggerated in order to clearly illustrate features of the embodiment(s). When a first layer is referred to as being "on" a second layer or "on" a substrate, it may not only refer to a case where the first layer is formed directly on the second layer or the substrate but may also refer to a case where a third layer exists between the first layer and the second layer or the substrate.

Figure 2:
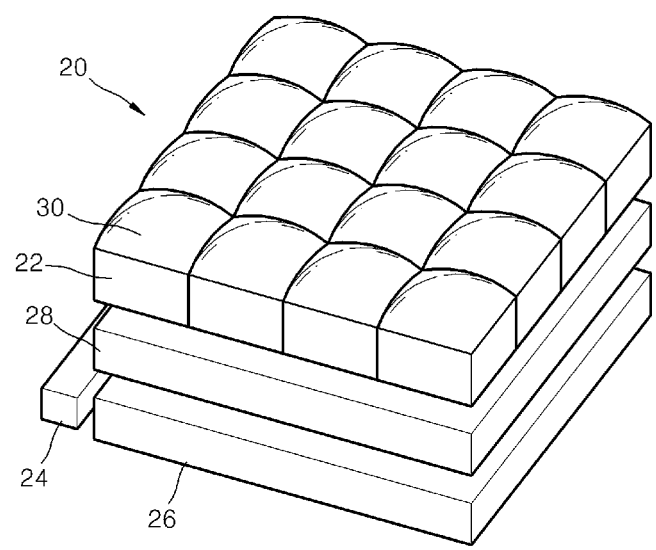
FIG. 2 is a schematic view illustrating an example of a light emission unit of the 3D image display apparatus illustrated in FIG. 1.
Figure 3:
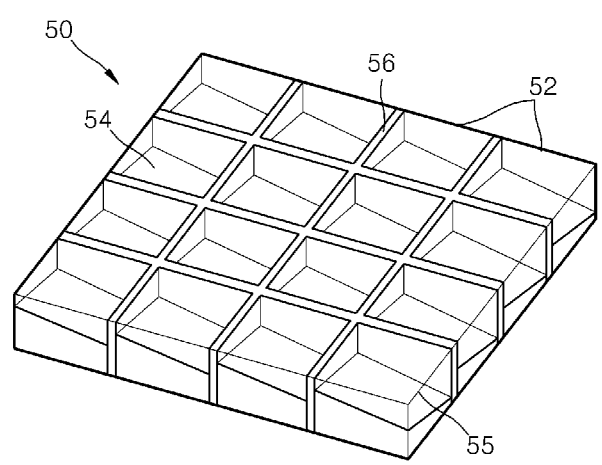
FIG. 3 is a schematic view illustrating an example of an active prism array of the 3D image display apparatus illustrated in FIG. 1.

A 3D image display apparatus according to an example embodiment divides visual fields for images being respectively presented to the left and right eyes by adjusting a direction in which light is emitted. As a result, the 3D image display apparatus may a 3D image may be displayed. FIG. 1 is a schematic view illustrating a 3D image display apparatus 10 according to an example embodiment. FIG. 2 is a schematic view illustrating an example of a light emission unit 20 of the 3D image display apparatus 10 illustrated in FIG. 1. FIG. 3 is a schematic view illustrating an example of an active prism array 50 of the 3D image display apparatus 10 illustrated in FIG. 1.

Referring to FIG. 1, the 3D image display apparatus 10 includes a light emission unit 20, an active prism array 50 that changes an angle of light emitted from the light emission unit 20, and a display panel 70 on the active prism array 50 that displays an image according to an input image signal.

The light emission unit 20 includes one or more cells 22 as shown in FIG. 2. Each of the cells 22 respectively adjusts a direction in which light is emitted. The cells 22 may be aligned two-dimensionally. A number and size of the cells 22 may vary according to a size, a pixel number, and a resolution of the 3D image display apparatus 10.

An incidence angle of light that is incident to the active prism array 50 may be changed by adjusting the direction in which light is emitted from the light emission unit 20. Then, the direction in which light is emitted may be secondarily adjusted by the active prism array 50.

Each of the cells 22 of the light emission unit 20 may independently and selectively adjust the direction in which light is emitted from the 3D image display apparatus 10. For example, an amount of the cells 22 may be equal to an amount of pixels of the display panel 70 to correspond to each other. In another example, each of the cells 22 may correspond to one or more pixels.

The light emission unit 20 includes a light array to selectively turn on or turn off a supply of light. The light array includes a light source 24, a light guide plate 26 to guide light emitted from the light source 24, and a shutter array 28 on the light guide plate 26. A lens array 30 is on the shutter array 28. A space layer 29 is between the lens array 30 and the shutter array 28 to ensure a focal distance. The space layer 29 may be formed of a material having a refractive index that is equal to a refractive index of the lens array 30. The space layer 29 may be formed integrally with the lens array 30.

The light source 24 may include a cold cathode fluorescent lamp (CCFL), a light emitting diode (LED), or an organic light emitting diode (OLED), but is not limited thereto. In addition, although FIG. 1 illustrates the light source 24 as an edge-type light source, in which light is irradiated from a side of the 3D image display apparatus 10, a direct-type light source, in which light is irradiated from below the 3D image display apparatus 10, may also be used.

The light guide plate 26 may have a scattering type light emission pattern.

The shutter array 28 includes one or more shutters in each of the cells 22. The shutters may be arranged in a one-dimensional or two-dimensional structure. For example, the shutter array 28 includes first to fourth shutters 28a, 28b, 28c, and 28d. The first to fourth shutters 28a, 28b, 28c, and 28d may be linearly aligned. Alternatively, the shutters may be aligned in an n×n arrangement, where n is a natural number, or in an n×m arrangement, where n and m are natural numbers. The first to fourth shutters 28a, 28b, 28c, and 28d may include a liquid crystal shutter, an electric wetting shutter, or a frustrated total internal reflection (FTIR) shutter. The FTIR shutter uses recycled light to reduce power consumption.

The lens array 30 includes lenses corresponding to each of the cells 22. The shutter array 28 may be on a focal plane of the lens array 30. For example, when the cells 22 have a two-dimensional structure, the lens array 30 may also have a two-dimensional structure.

A diffusion plate (not shown) to uniformly diffuse light emitted from the light guide plate 26, a prism sheet (not shown) to correct a light proceeding path, and a brightness improving film (not shown) may be between the shutter array 28 and the light guide plate 26. Although not shown in the drawings, a prism light emission pattern to collimate light may be on a surface of the light guide plate 26 facing toward the display panel 70 or a surface of the light guide plate 26 facing away from the display panel 70. The prism light emission pattern is well known in the art.

The light emitted from the light source 24 may be spread to an entire surface of the light guide plate 26. As a result, the light source 24 becomes a surface light source. The light emitted from the light guide plate 26 toward the display panel 70 may be turned on/off according to opening/closing operations of the shutter array 28.

In addition, the light emission unit 20 may include a direction adjustor to limit a proceeding direction of light emitted from the light array. The lens array 30 may function as the direction adjustor to limit the proceeding direction of light passing through the shutter array 28. Further, the proceeding direction of the light may be controlled cooperatively through an opening of shutters in certain locations and the lens array 30.

For example, when the first shutter 28a is opened and the other shutters are closed in an example cell of the cells 22 of FIG. 1, the light may proceed through the first shutter 28a toward a left side of the example cell. Alternatively, if the second shutter 28b or the third shutter 28c is opened and the other shutters are closed in an example cell of the cells 22 of FIG. 1, the light may proceed through the second shutter 28b or the third shutter 28c toward a center of the example cell. Alternatively, if the fourth shutter 28d is opened and the other shutters are closed in an example cell of the cells 22 of FIG. 1, the light may proceed through the fourth shutter 28d toward a right side of the example cell.

As described above, the direction in which light is emitted may be adjusted by the cells 22 in various directions by using a combination of one or more open shutters of a cell and a corresponding lens of the cell. As a result, the emitted light may be incident to the active prism array 50.

The range of the incidence angle of light incident to the active prism array 50 may vary according to the number and the arrangement of the shutters of the shutter array 28.

Referring to FIG. 3, the active prism array 50 is partitioned into one or more prism units 52. The angle by which light is emitted may be adjusted by controlling an inclination of a refracting surface 54 included in each of the prism units 52 according to an electric signal. The active prism array 50 may include an electric wetting device. The prism units 52 are partitioned by barrier walls 56. Each of the prism units 52 includes a prism 55.

In the active prism array 50, the prism units 52 may be aligned two-dimensionally in the same arrangement as the cells 22 of the light emission unit 20.

Figure 4:
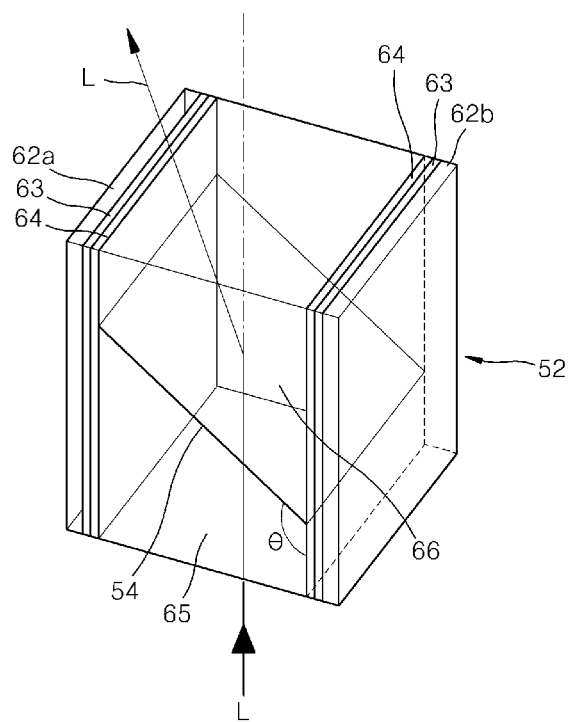
FIG. 4 is a schematic view illustrating an example of a prism unit of an active prism array of the 3D image display apparatus illustrated in FIG. 1.
Figure 5:
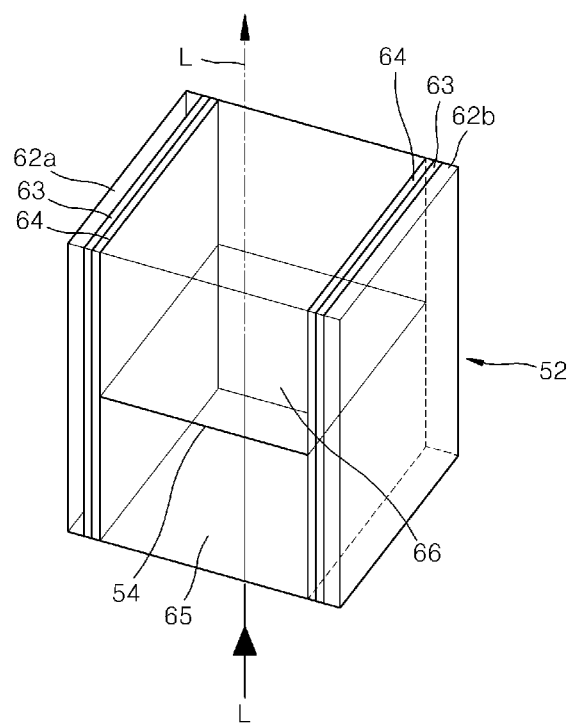
FIG. 5 is a diagram illustrating an example of an operation of a prism unit of an active prism array of the 3D image display apparatus illustrated in FIG. 1.

FIG. 4 is a schematic view illustrating an example of a prism unit 52 of the active prism array 50 of the 3D image display apparatus illustrated in FIG. 1. FIG. 5 is a diagram illustrating an example of an operation of a prism unit of an active prism array of the 3D image display apparatus illustrated in FIG. 1.

Referring to FIG. 4, the prism unit 52 includes a first electrode 62a and a second electrode 62b that face each other. A first medium 65 and a second medium 66, which have different refractive indices, are between the first electrode 62a and the second electrode 62b. For example, the first medium 65 may be a polarizing liquid such as water, and the second medium 66 may be a non-polar liquid such as oil. A boundary between the first medium 65 and the second medium 66 becomes the refracting surface 54.

Hydrophobic layers 64 are respectively on an inner wall of the first electrode 62a and an inner wall of the second electrode 62b. An insulating layer 63 is between the first electrode 62a and the hydrophobic layer 64 and between the second electrode 62b and the hydrophobic layer 64. Alternatively, the insulating layer 63 may be formed of a hydrophobic material. In this case, a separate hydrophobic layer is not required.

According to the example embodiment, the prism unit 52 is driven by using two electrodes; however, the example embodiment is not limited thereto. For example, the prism unit 52 may be driven by using four electrodes respectively disposed on four side walls of the prism unit 52.

If a voltage is not applied to the first electrode 62a and the second electrode 62b, the first medium 65 is inclined at a high contact angle $\theta$ with respect to the hydrophobic layer 64. When predetermined voltages are respectively applied to the first electrode 62a and the second electrode 62b, the contact angle between the hydrophobic layer 64 and the first medium 65 may be reduced. In addition, the respective application of voltages to the first electrode 62a and the second electrode 62b serves to change the inclination of the refracting surface 54. When the inclination of the refracting surface 54 is changed, the direction in which light is emitted also changes. As such, the direction in which light is emitted may be controlled by turning on/off of the respective voltages applied to the first electrode 62a and the second electrode 62b or by adjusting the magnitude of the respective voltages.

In FIG. 4, light L is refracted on the refracting surface 54 to proceed toward the left side. Referring to the example illustrated in FIG. 5, when predetermined voltages are applied respectively to the first electrode 62a and the second electrode 62b, the refracting surface 54 becomes parallel to the incidence surface of the prism unit 52. In this case, the light L passes through the refracting surface 54 at a right angle with respect to the refracting surface 54 and the incidence surface of the prism unit 52. The inclination of the refracting surface 54 may vary according to the magnitude and direction of the respective voltages applied to the first electrode 62a and the second electrode 62b. As previously noted above, when the inclination of the refracting surface 54 is changed, the direction in which light is emitted also changes.

When respective voltages are applied to the first electrode 62a and the second electrode 62b, a difference between the refractive indices of the first medium 65 and the second medium 66 may be modified or increased. As a result, the modification of the difference between the refractive indices of the first medium 65 and the second medium 66 has the effect of modifying or increasing the contact angle between the first medium 65 or the second medium 66 and the hydrophobic layer 64. As a result, the light proceeding angle may be changed significantly, thereby influencing the direction in which light is emitted.

In general, a medium that is used to refract light may have a high refractive index and, thus, a high viscosity. Further, the refractive index of the medium having high viscosity may significantly change according to the wavelength. Thus, even though a medium having a high refractive index is used in refracting light, changing the light proceeding direction by adjusting a contact angle in a prism unit may be difficult. Furthermore, electric wetting characteristics may deteriorate when the contact angle between the second medium 66 and the hydrophobic layer 64 is increased. Thus, a range within which the angle of light emission may be changed by the active prism array 50 may be about ±10°.

According to the example embodiment, the range of incidence angle of the light that is incident to the active prism array 50 may be increased by adjusting the angle by which light is emitted from the light emission unit 20. In addition, the refraction angle of the light may be changed by the active prism array 50 as noted above. Accordingly, the range within which the angle of light emission may be changed may be increased. A viewing angle of the 3D image display apparatus 10 may be widened by increasing the range within which the angle of light emission may be changed.

FIGS. 4 and 5 show an example of using electric wetting characteristics in the active prism array 50 to adjust the direction in which light is emitted. However, the example embodiment is not limited thereto. For example, if an image is formed using polarized light, the direction in which light is emitted may be adjusted using liquid crystal. In this case, an arrangement of liquid crystal molecules is changed according to a magnitude of an electric field formed by the respective voltages applied to the electrodes, thereby serving to change the refractive index of the liquid crystal.

Light emitted from the light emission unit 20 and the active prism array 50 may be modulated in the display panel 70 to display images. The display panel 70 includes one or more pixels. Each of the pixels may adjust light transmittance to form an image. The display panel 70 may be a LCD panel. The display panel 70 includes a first substrate 71, a liquid crystal layer 72, and a second substrate 73.

The direction in which light generated from the light source 24 is emitted is adjusted by the light emission unit 20 and the active prism array 50. A gray scale of the light is expressed by the display panel 70. Thus, an image is formed. For example, if the light emission unit 20 and the active prism array 50 transmit light to the left eye in a first frame and transmit light to the right eye in a second frame, a 3D image may be displayed. Alternatively, if the light emission unit 20 and the active prism array 50 transmit light to both the left and right eyes, a 2D image may also be displayed. For example, if all shutters of the shutter array 28 are opened in the light emission unit 20, and the refracting surfaces of the prism units 52 of the active prism array 50 become parallel to the incidence surfaces of the prism units 52 of the active prism array 50, a 2D image may be displayed. Alternatively, the 2D image may also be displayed by opening shutters of the shutter array 28 located at the same position in each of the cells 22. By using the 3D image display apparatus 10 according to the example embodiment, 3D images may be converted into 2D images, and vice versa.

A controller 80 of the 3D image display apparatus 10 may include data about relations between the opening and closing operations of the shutters of the shutter array 28 of the light emission unit 20 and the inclination adjustment of the refracting surface of the prism units of the active prism array 50. The direction in which light is emitted may be adjusted in various directions, for example, in the left-to-right direction, the up-and-down direction, and the diagonal direction of the 3D image display apparatus 10 by the cooperation of the shutter array 28 and the active prism array 50.

Figure 6:
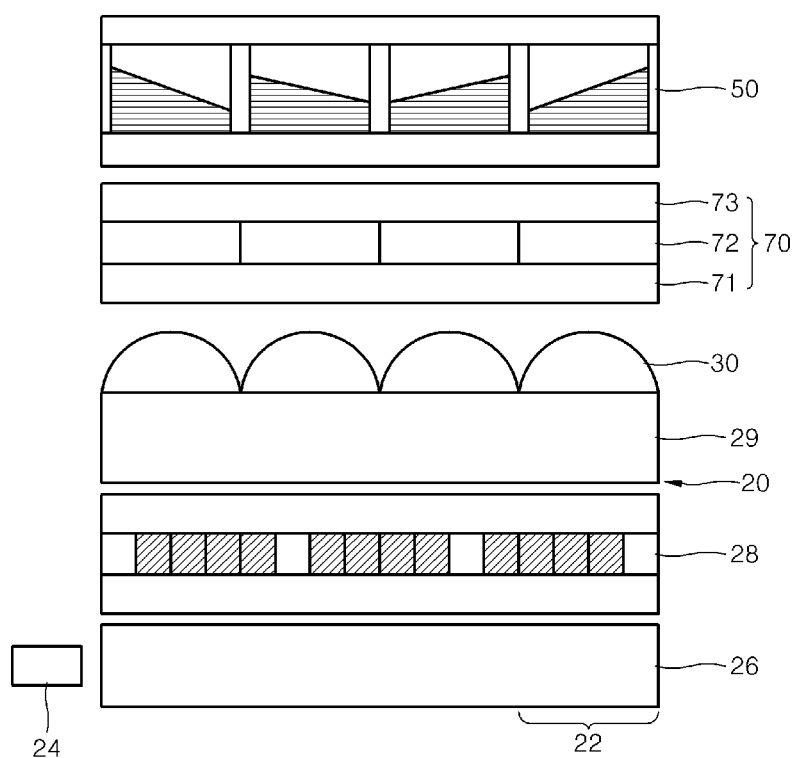
FIG. 6 is a schematic view illustrating the 3D image display apparatus illustrated in FIG. 1 when a display panel location is changed.

FIG. 6 is a schematic view illustrating the 3D image display apparatus 10 illustrated in FIG. 1 in which the locations of the display panel 70 and the active prism array 50 are exchanged. As such, the display panel 70 in FIG. 6 is between the light emission unit 20 and the active prism array 50.

Figure 7:
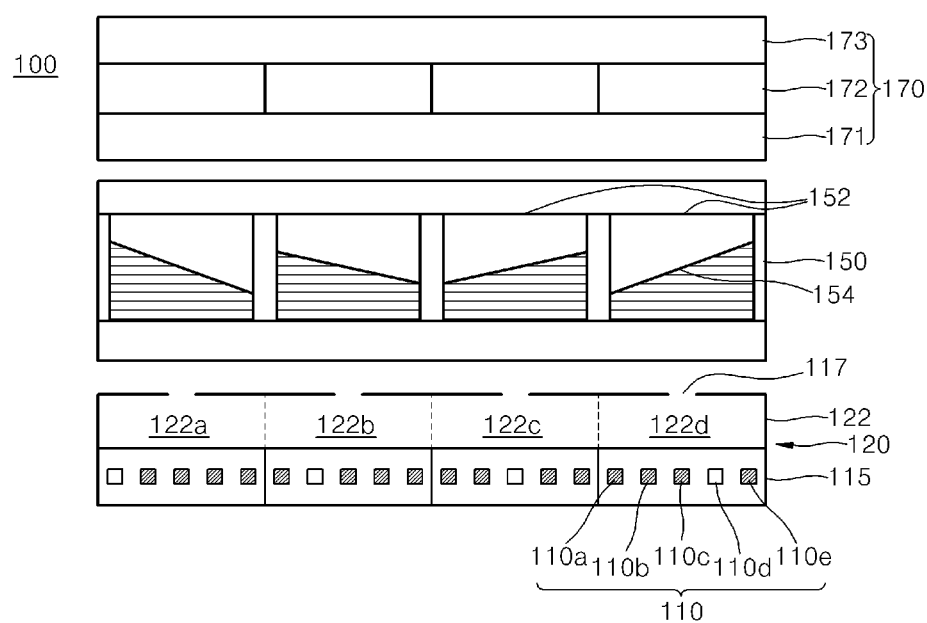
FIG. 7 is a schematic view illustrating a 3D image display apparatus according to another example embodiment.

FIG. 7 is a schematic view illustrating a 3D image display apparatus 100 according to another example embodiment. The 3D image display apparatus 100 includes a light emission unit 120 and an active prism array 150 that cooperate to change an angle by which light is emitted from the light emission unit 120. A display panel 170 that displays an image according to an input image signal is on the active prism array 150.

The light emission unit 120 includes one or more cells 122 as shown in FIG. 7. Each of the cells 122 may respectively adjust a direction in which light is emitted. The cells 122 may be aligned two-dimensionally, and an amount and a size of the cells 122 may vary according to a size, a pixel number, and a resolution of the 3D image display apparatus 100. The incidence angle of the light that is incident to the active prism array 150 may be changed by adjusting the angle by which light is emitted from the light emission unit 120. In addition, the direction in which light is emitted is adjusted by the active prism array 150, thereby serving to widen a viewing angle of the 3D image display apparatus 100.

Each of the cells 122 of the light emission unit 120 may independently and selectively adjust the direction in which light is emitted. For example, an amount of the cells 122 may be equal to an amount of corresponding pixels of the display panel 170. Further, each of the cells 122 may correspond to one or more pixels.

The light emission unit 120 includes a light source array 115 in which one or more light sources 110 are aligned. A pin hole 117 is formed by each of the cells 122 of the light source array 115. The light source array 115 may be a light emitting diode (LED) or an organic light emitting diode (OLED).

In the light source array 115, the light sources 110 may be aligned in a one-dimensional or two-dimensional structure. For example, the light source array 115 includes first to fifth light sources 110a, 110b, 110c, 110d, and 110e. The light proceeding direction may be affected by the cooperation of one or more of light sources that are turned on among the light sources of the light source array 115, and the pin hole 117 corresponding to the light sources that are turned on.

For example, the cells 122 include a first cell 122a, a second cell 122b, a third cell 122c, and a fourth cell 122d. When the first light source 110a is turned on, and the other light sources are turned off in the first cell 122a, the light emitted from the first light source 110a may proceed from a left side of the first cell 122a to the extent allowed by the pin hole 117 of the first cell 122a. When the second light source 110b is turned on, and the other light sources are turned off in the second cell 122b, the light emitted from the second light source 110b may proceed mostly from a left side of the second cell 122b to the extent allowed by the pin hole 117 of the second cell 122b. When the third light source 110c is turned on, and the other light sources are turned off in the third cell 122c, the light may proceed toward the center of FIG. 7 through the pin hole 117 of the third cell 122c. When the fourth light source 110d is turned on, and the other light sources are turned off in the fourth cell 122d, the light may proceed mostly from a right side of the fourth cell 122d to the extent allowed by the pin hole 117 of the fourth cell 122d. As such, the direction in which light is emitted may be adjusted by using a combination of the location of the light sources 110 that are turned on and the pin hole 117 in each of the cells 122. That is, the light may be transmitted in the desired direction by using relative locations between the pin hole 117 and the light sources that are turned on. Two or more light sources may also be turned on in the light source array 115 of each of the cells 122 in order to adjust the amount of light.

The range of the incidence angle of light incident to the active prism array 150 may be adjusted by the light emission unit 120. The active prism array 150 is partitioned into one or more prism units 152. The angle by which light is emitted may be adjusted by controlling an inclination of refracting surfaces 154 in each respective prism unit 152 according to an electric signal. The active prism array 150 may include an electric wetting device. In the active prism array 150, the prism units 152 may be aligned two-dimensionally in the same arrangement as the cells 122 of the light emission unit 120. Since the active prism array 150 is substantially identical to that described above with reference to FIGS. 3, 4, and 5, descriptions thereof will be omitted herein.

The light emitted from the light emission unit 120 and the active prism array 150 may be modulated in the display panel 170 to display an image. The display panel 170 includes one or more pixels. Each of the pixels may control light transmittance to form an image. The display panel 170 may be a LCD panel. The display panel 170 includes a first substrate 171, a liquid crystal layer 172, and a second substrate 173. The display panel 170 may be between the light emission unit 120 and the active prism array 150 instead of being disposed on the active prism array 150.

For example, the range of incidence angle of the light that is incident to the active prism array 150 may be increased by adjusting the angle by which light is emitted from the light emission unit 120. In addition, the refraction angle of the light may be changed by the active prism array 150. Accordingly, the range within which the angle of light emission may be changed may be increased. A viewing angle of the 3D image display apparatus 100 may be increased by increasing the range within which the angle of light emission may be changed.

By the cooperation of the light emission unit 120 and the active prism array 150, the light is transmitted to the left eye in a first frame and the light is transmitted to the right eye in a second frame. Thus, a 3D image may be displayed. A 3D image of multi-views may also be displayed. A 2D image may also be displayed by turning on the light sources located at the same position of light source array 115 in each of the cells 122 and making the refracting surfaces 154 of the prism units 152 of the active prism array 150 become parallel to the incidence surfaces of the prism units 152 of the active prism array 150. As such, the 2D image may be converted into the 3D image, and vice versa. In addition, since an entire region of the display panel 170 is used to display the left eye image and the right eye image when displaying the 3D image, the 3D image may be displayed without degrading the resolution of the image.

Figure 8:
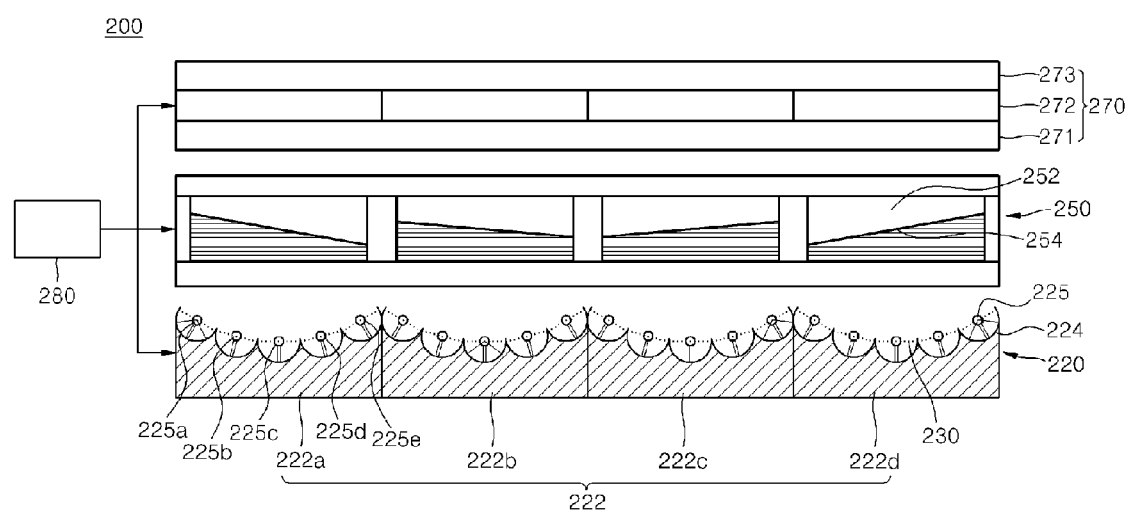
FIG. 8 is a schematic view illustrating a 3D image display apparatus according to yet another example embodiment.

FIG. 8 is a schematic view illustrating a 3D image display apparatus 200 according to yet another example embodiment. The 3D image display apparatus 200 includes a light emission unit 220 and an active prism array 250 that changes an angle by which light is emitted from the light emission unit 220. A display panel 270 that displays an image according to an input image signal is on the active prism array 250.

The light emission unit 220 includes one or more cells 222. Each of the cells 222 includes a reflection unit 224 and a light source 225 corresponding to the reflection unit 224. The reflection unit 224 has a curved surface and may include a material to reflect light emitted from the light source 225. The light source 225 may include a LED or an OLED. The reflection unit 225 may be arranged in a three-dimensional structure, e.g., on the curved surface, in each of the cells 222. According to this arrangement, forward directions of the reflection units 224 become different from each other. As a result, light may be reflected by the reflection units 224 in differing directions. For example, the reflection unit 224 of each of the cells 222 may be arranged in an inversion-symmetric structure. Further, each of the cells 222 may collectively adjust the direction in which light is emitted by turning-on/turning-off the light source 225.

The cells 222 include a first cell 222a, a second cell 222b, a third cell 222c, and a fourth cell 222d. The light source 225 includes first to fifth light sources 225a, 225b, 225c, 225d, and 225e in each cell 222. For example, the direction in which light is emitted may be adjusted by turning on the first light source 225a and turning off the other light sources in the first cell 222a, turning on the second light source 225b and turning off the other light sources in the second cell 222b, turning on the third light source 225c and turning off the other light sources in the third cell 222c, and turning on the fourth light source 225d and turning off the other light sources in the fourth cell 222d. The direction in which light is emitted in each of the cells 222 may be determined by the location of the light source 225 that has been turned on.

A controller 280 of the 3D image display apparatus 200 may include data about relations between on-off operations of the light sources 225 and the direction in which light is emitted in each of the cells 222. The direction in which light is emitted may be adjusted in various directions, for example, in the left-to-right direction, the up-and-down direction, and the diagonal direction of the 3D image display apparatus 200, according to the arrangement of the reflection unit 224.

The reflection unit 224 may be formed as a parabolic mirror that is configured to reflect the light emitted from the light source 225 as parallel light when the light source 225 is located at a focal point of the parabolic mirror. The reflection unit 224 may reflect the light emitted from each corresponding light source 225 as collimated light. A virtual line 230 connecting the light sources 225 may be a curve in the cross-sectional view of the light source 225. As described above, the direction in which light is emitted may be adjusted by using the combination of the locations of the light source 225 and the reflection unit 224.

The range of the incidence angle of light incident to the active prism array 250 may be adjusted by the light emission unit 220. The active prism array 250 is partitioned into one or more prism units 252, and the angle by which light is emitted may be adjusted by controlling an inclination of a refracting surface 254 according to an electric signal. The active prism array 250 may include an electric wetting device. In the active prism array 250, the prism units 252 may be aligned two-dimensionally in the same arrangement as the cells 222 of the light emission unit 220. Since the active prism array 250 is substantially identical to that described above with reference to FIGS. 3, 4, and 5, descriptions thereof will be omitted herein.

The light emitted from the light emission unit 220 and the active prism array 250 is modulated in the display panel 270 to display an image. The display panel 270 includes one or more pixels. Each of the pixels may control light transmittance to form an image. The display panel 270 may be a LCD panel. The display panel 270 includes a first substrate 271, a liquid crystal layer 272, and a second substrate 273. The LCD panel is well known in the art, and thus descriptions thereof will be omitted herein. The display panel 270 may be between the light emission unit 220 and the active prism array 250 instead of being on the active prism array 250.

The range of incidence angle of the light that is incident to the active prism array 250 is increased by adjusting the angle by which light is emitted from the light emission unit 220. In addition, the refraction angle of the light is changed by the active prism array 250. Accordingly, the range within which the angle of light emission may be changed may be increased. A viewing angle of the 3D image display apparatus 200 may be increased by increasing the range within which the angle of light emission may be changed.

As described above, a 3D image may be displayed by separately transmitting the light to the left and right eyes by adjusting the light proceeding direction using the light emission unit 220 and the active prism array 250. Further, the left eye image and the right eye image are displayed in a time-sequential manner to display the 3D image without degrading the resolution.

In a first frame, the location of the light source 225 of the light emission unit 220 that is turned on is adjusted in each of the cells 222. In addition, the inclination of the refracting surface 254 of the active prism array 250 is adjusted so that the light is transmitted to the left eye. As a result, the display panel 270 forms the image for the left eye.

Further, in a second frame, the location of the light source 225 of the light emission unit 220 that is turned on is adjusted in each of the cells 222. The inclination of the refracting surface 254 of the active prism array 250 is adjusted so that the light is transmitted to the right eye. As a result, the display panel 270 forms the image for the right eye. The viewing angle may be widened by increasing the range within which the angle of light emission may be changed by the light emission unit 220 and the active prism array 250. For example, a viewing angle of the light may be widened by ±20 or greater.

Meanwhile, a 2D image may also be displayed by turning on the light source 225 located at the same position, for example, at the center, in each of the cells 222 and making the refracting surface 254 of the active prism array 250 flat so that the light is transmitted toward the front surface of the 3D image display apparatus 200. As such, the 3D image may be converted into the 2D image, and vice versa, by respectively adjusting the direction in which light is emitted in each of the cells 222.

According to the teachings above, there is provided a 3D image display apparatus in which a range within which the angle of light emission may be changed may be increased in the 3D image display apparatus by changing the angle by which light is emitted by two stages. In addition, a viewing angle of a 3D image display apparatus may be widened by increasing the range within which the angle of light emission may be changed.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A 3D image display apparatus, comprising:
a light emission unit comprising one or more cells, the cells being configured to adjust a first direction in which light is emitted;
an active prism array on the light emission unit, the active prism array comprising one or more prism units corresponding to the cells, the active prism array being configured to adjust an inclination of a refracting surface of each of the prism units to adjust a second direction in which light is refracted by the refracting surface; and
a display panel configured to modulate light that passes through the active prism array according to an image signal to form an image, wherein:
the light emission unit is configured to adjust an angle by which light is emitted from the light emission unit,
a range of incidence angle of light incident to the active prism array dependent upon the adjusted angle, and
a range within which an angle of light emission is changed is dependent upon the range of incidence angle of light and the adjusted angle.

2. The 3D image display apparatus of claim 1, wherein the adjusted inclination of the refracting surface of each of the prism units is dependent upon the adjusted direction in which light is emitted.

3. The 3D image display apparatus of claim 1, wherein the second direction in which light is emitted from the active prism array is dependent upon the adjusted direction in which light is emitted and the adjusted inclination of the refracting surface of each of the prism units.

4. The 3D image display apparatus of claim 1, wherein the display panel is between the light emission unit and the active prism array.

5. The 3D image display apparatus of claim 1, wherein the display panel is on the light emission unit and the active prism array.

6. The 3D image display apparatus of claim 1, wherein the light emission unit comprises a light guide plate configured to guide light emitted from a light source, a shutter array on the light guide plate, the shutter array comprising one or more shutters, the shutters being grouped to respectively correspond to each of the cells, each of the shutters being independently openable and closeable, and a lens array on the shutter array.

7. The 3D image display apparatus of claim 6, wherein the light emission unit further comprises the light source.

8. The 3D image display apparatus of claim 6, wherein the shutter array comprises a liquid crystal shutter, an electric wetting shutter, or a frustrated total internal reflection (FTIR) shutter.

9. The 3D image display apparatus of claim 6, wherein the shutter array is arranged in a two-dimensional structure.

10. The 3D image display apparatus of claim 6, wherein the shutter array is on a focal plane of the lens array.

11. The 3D image display apparatus of claim 6, wherein the lens array comprises one or more lenses corresponding to each of the cells, each of the lenses being configured to limit a proceeding direction of light emitted from a respective grouping of the shutters.

12. The 3D image display apparatus of claim 6, further comprising:
a controller having data, the data comprising relations between opening and closing operations of the shutters and the adjusted inclination of the refracting surface of each of the prism units.

13. The 3D image display apparatus of claim 1, wherein the light emission unit comprises a light source array comprising one or more light sources, the light sources being grouped to respectively correspond to each of the cells, each of the light sources being independently turned on and turned off, and a pin hole array comprising one or more pin holes corresponding to each of the cells, each of the pin holes being configured to limit a proceeding direction of light emitted from a respective grouping of the light sources.

14. A 3D image display apparatus, comprising:
a light emission unit comprising one or more cells, the cells being configured to adjust a first direction in which light is emitted;
an active prism array comprising one or more prism units corresponding to the cells, the active prism array being configured to adjust an inclination of a refracting surface of each of the prism units to adjust a second direction in which light is refracted by the refracting surface; and
a display panel configured to modulate light that passes through the active prism array according to an image signal to form an image,
wherein the light emission unit comprises one or more reflection units grouped in a curved surface shape in each of the cells, each of the reflection units having a curved surface shape, and each of the reflection units having a light source disposed thereon.

15. The 3D image display apparatus of claim 14, wherein each of the reflection units reflect light emitted from the light source as collimated light.

16. The 3D image display apparatus of claim 14, wherein the light source of each of the reflection units is independently turned on and turned off.

17. A 3D image display apparatus, comprising:
a light emission unit comprising one or more cells, the cells being configured to adjust a first direction in which light is emitted;
an active prism array comprising one or more prism units corresponding to the cells, the active prism array being configured to adjust an inclination of a refracting surface of each of the prism units to adjust a second direction in which light is refracted by the refracting surface; and
a display panel configured to modulate light that passes through the active prism array according to an image signal to form an image,
wherein each of the prism units comprises a first electrode and a second electrode facing each other, a first hydrophobic layer on an inner wall of the first electrode, a second hydrophobic layer on an inner wall of the second electrode, a first medium between the first electrode and the second electrode, a second medium between the first electrode and the second electrode, and the second medium having a refractive index that is different from a refractive index of the first medium.

18. The 3D image display apparatus of claim 17, wherein the first medium comprises a polarizing liquid, and
wherein the second medium comprises a non-polar liquid.

19. The 3D image display apparatus of claim 17, wherein the refracting surface comprises a boundary between the first medium and the second medium.

* * * * *